(12) United States Patent
Ergun

(10) Patent No.: US 10,258,433 B2
(45) Date of Patent: Apr. 16, 2019

(54) DEVICE FOR INTRA-ORAL APPLICATIONS TO REPOSITION MANDIBULAR JAW

(71) Applicant: Mustafa Ali Ergun, Eden Prairie, MN (US)

(72) Inventor: Mustafa Ali Ergun, Eden Prairie, MN (US)

(*) Notice: Subject to any disclaimer, the term of this patent is extended or adjusted under 35 U.S.C. 154(b) by 0 days.

(21) Appl. No.: 15/571,283

(22) PCT Filed: Nov. 10, 2016

(86) PCT No.: PCT/US2016/061230
§ 371 (c)(1),
(2) Date: Nov. 2, 2017

(87) PCT Pub. No.: WO2017/083458
PCT Pub. Date: May 18, 2017

(65) Prior Publication Data
US 2018/0235733 A1 Aug. 23, 2018

Related U.S. Application Data

(60) Provisional application No. 62/253,682, filed on Nov. 11, 2015.

(51) Int. Cl.
*A61C 7/36* (2006.01)
*A61C 7/18* (2006.01)

(52) U.S. Cl.
CPC . *A61C 7/36* (2013.01); *A61C 7/18* (2013.01)

(58) Field of Classification Search
CPC .... A61C 7/00; A61C 7/18; A61C 7/36; A61C 7/282; A61C 7/06; A61F 5/56; A61F 5/566; A61F 2005/563; A63B 71/085
(Continued)

(56) References Cited

U.S. PATENT DOCUMENTS 5,848,891 A  12/1998 Eckhart et al.
6,099,304 A  8/2000 Carter
(Continued)

FOREIGN PATENT DOCUMENTS

WO  WO2015/157472  10/2015

OTHER PUBLICATIONS

International Application Serial No. PCT/US2016/061230, International Search Report dated Mar. 2, 2017, 4 pgs.
(Continued)

*Primary Examiner* — Edward Moran
*Assistant Examiner* — Drew S Folgmann (57) ABSTRACT

An orthodontic appliance for moving the mandibular jaw relative to the maxillary jaw in response to jaws being closed is described. The orthodontic appliance includes a first member and a second member which is disconnected from the first member when jaws are in open position. The first member is adapted to be fixedly attached to one of mandibular or maxillary dental arches, and the second member is adapted to be rotatingly coupled with the other one of mandibular or maxillary dental arches. The first member and second member are in vertical alignment. During the closure of dental arches, the second member contacts the first member, and the rotation of the second member is initiated. Rotation of the second member pushes the mandibular jaw in either anterior or posterior direction.

11 Claims, 11 Drawing Sheets

(58) Field of Classification Search
USPC .................................. 128/861; 433/6, 19, 24
See application file for complete search history.

(56) References Cited

U.S. PATENT DOCUMENTS

| | | | | |
|---|---|---|---|---|
| 6,113,390 | A * | 9/2000 | Sirney ..................... | A61C 7/36 433/19 |
| 6,394,799 | B1 | 5/2002 | Testa et al. | |
| 6,913,460 | B2 * | 7/2005 | Cleary .................... | A61C 7/36 433/17 |
| 2003/0232301 | A1 * | 12/2003 | Cleary .................... | A61C 7/36 433/19 |
| 2007/0190477 | A1 | 8/2007 | Sheikh et al. | |
| 2009/0126742 | A1 | 5/2009 | Summer | |
| 2012/0028208 | A1 * | 2/2012 | Cleary .................... | A61C 7/36 433/19 |

OTHER PUBLICATIONS

International Application Serial No. PCT/US2016/061230, Written Opinion dated Mar. 2, 2017.

\* cited by examiner

DEVICE FOR INTRA-ORAL APPLICATIONS TO REPOSITION MANDIBULAR JAW

CLAIM OF PRIORITY

This application is a U.S. National Stage Filling under 35 U.S.C. § 371 from International Application No. PCT/US2016/061230, entitled "DEVICE FOR INTRA-ORAL APPLICATIONS TO REPOSITION MANDIBULAR JAW-"filed on Nov. 10, 2016, and published as WO 2017/083458 A1 on May 18, 2017,which claims the benefit of priority under 35 U.S.C. § 119(e) to U.S. Provisional Application Ser. No. 62/253,682, titled "DEVICE FOR INTRA-ORAL APPLICATIONS TO REPOSITION MANDIBULAR JAW", to Mustafa Ergun, and filed on Nov. 11, 2015, which is incorporated, herein by reference in its entirety.

TECHNICAL FIELD

The invention relates generally, but not by way of limitation, to orthodontic devices.

BACKGROUND

Figure 1:
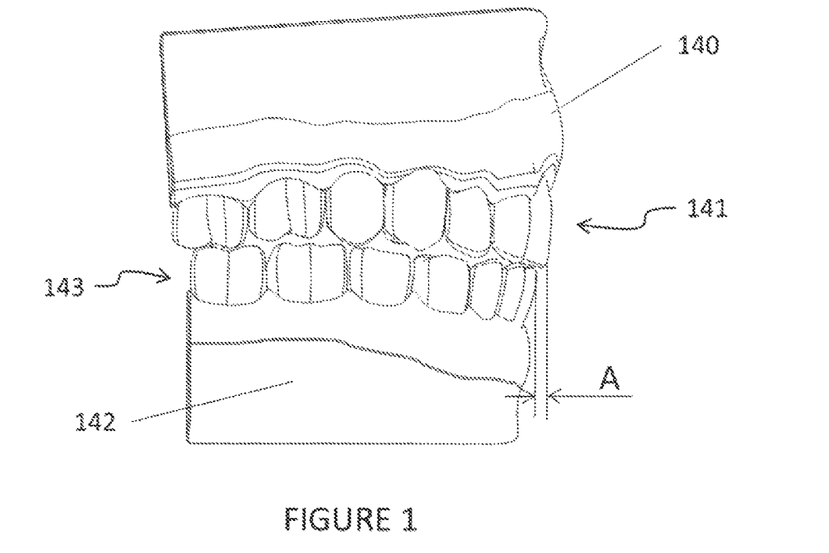
FIG. 1 illustrates the normal alignment of mandibular and maxillary jaws.
Figure 2:
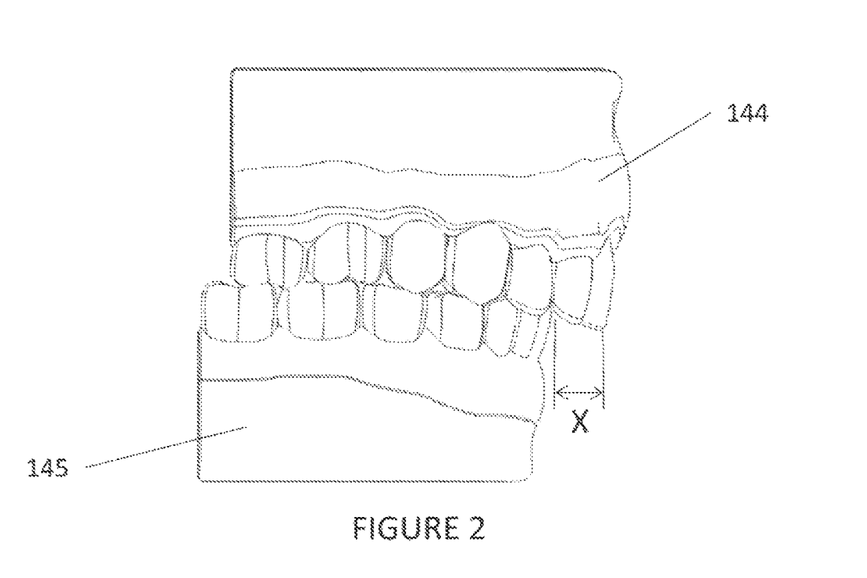
FIG. 2 illustrates the orientation of mandibular and maxillary jaws relative to each other in Class II malocclusion.
Figure 3:
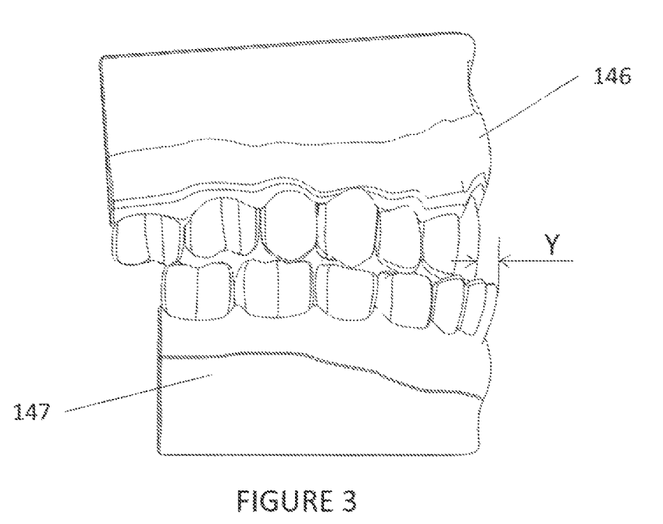
FIG. 3 illustrates the orientation of mandibular and maxillary jaws relative to each other in Class III malocclusion.

As illustrated in FIG. 1, human mouth includes an upper jaw bone or maxilla 140 and a lower jaw bone or mandible 142, both operationally linked to perform chewing function. A set of upper teeth 141, and a set of lower teeth 143 are located on the respective jaw bones. Generally, as shown in FIG. 1, maxilla 140 is protracted a certain distance (A) anteriorly with respect to mandible 142. A malocclusion where mandible 145 is positioned posteriorly with respect to maxilla 144 a certain distance (X) as illustrated in FIG. 2 is classified as Class II malocclusion. On the other hand, a malocclusion where mandible 147 is positioned anteriorly with respect to maxilla 146 a certain distance (Y) as illustrated in FIG. 3 is classified as Class III malocclusion.

Figure 4:
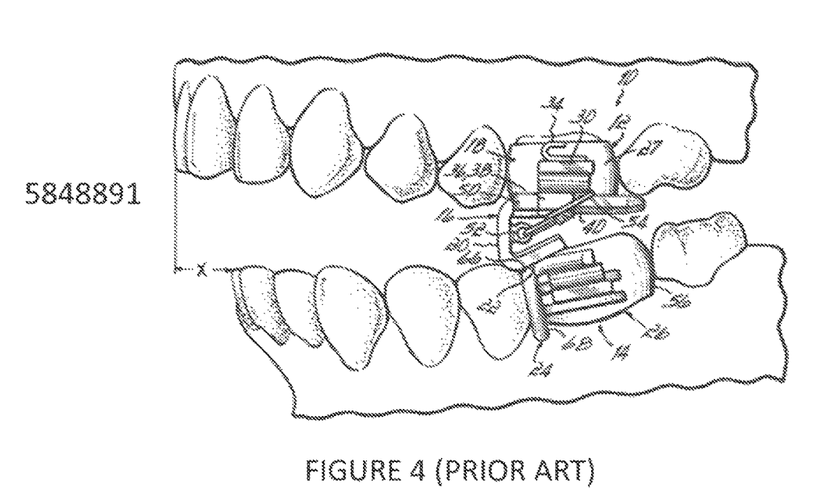
FIG. 4 illustrates Class II malocclusion and an example of an orthodontic appliance to correct it.
Figure 5:
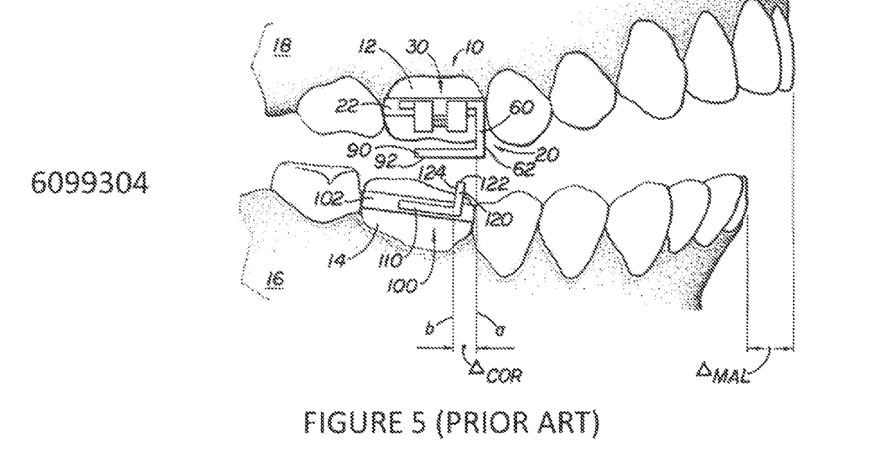
FIG. 5 illustrates Class II malocclusion and another example of an orthodontic appliance to correct it.
Figure 6:
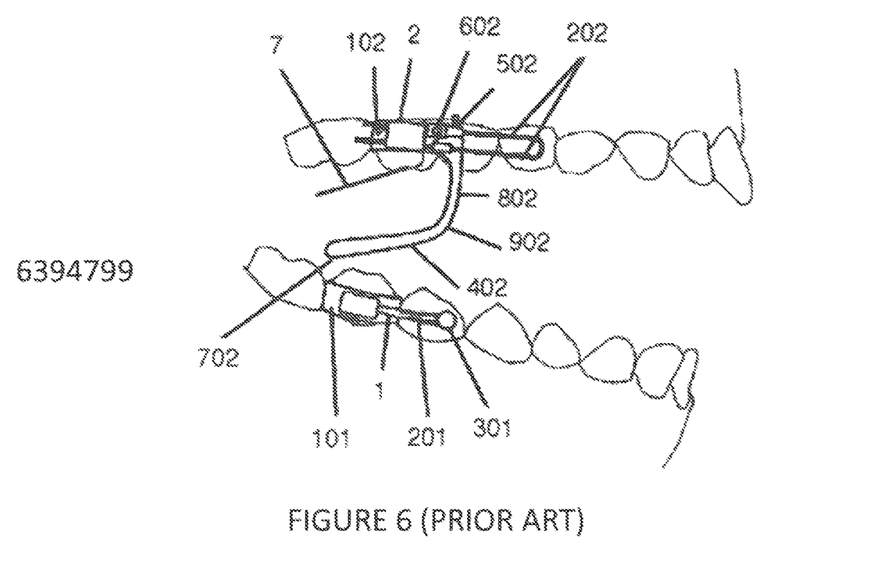
FIG. 6 illustrates Class II malocclusion and yet another example of an orthodontic appliance to correct it.

Positioning devices between upper and lower jaws are commonly used in orthodontics to treat patients with Class II malocclusions. Examples of such devices are shown in FIGS. 4 to 6. Common feature of these devices is that they are composed of two separate assemblies. Each assembly is attached to one of either maxillary or mandibular jaws. When the jaws are open, two assemblies are separated from each other. They come in contact when the jaws are closed, and a forward moving force is applied to the mandibular jaw to reposition it relative to the maxillary jaw.

Existing, positioning devices for intraoral applications, in general, has obstruction elements which contact when the jaws are proximate to each other in their uncorrected orientation, and prevent jaws from being fully closed. To close the jaws completely, mandibular jaw is pushed to its corrected position to clear the obstruction surface, and only then, jaws can be fully closed. This requires a controlled action by the patient, and it can be annoying especially in early stages of the treatment. A fluid motion that forces the mandibular jaw to its correct position as the jaws are being closed would receive better acceptance by the patients.

OVERVIEW

Embodiments of the invention include an orthodontic appliance that can be attached to maxillary and mandibular jaws to apply a moving force to mandibular jaw to reposition it relative to the maxillary jaw to correct patient's bite. Similar systems with slight variations or attachment points to patient's jaws can be used to correct various jaw discrepancies such as Class II or Class III malocclusions.

Orthodontic appliance includes a first member and a second member. The member is fixedly attached to one of mandibular or maxillary jaws, and the second member is rotatingly coupled with the other one of mandibular or maxillary jaws. The first member and the second member are completely disconnected from each other when jaws are open. When jaws are within close proximity of each other in uncorrected orientation of jaws, the first member and the second member contact each other at two distinct points creating a first contact force and a second contact force wherein the first contact force causes the second member rotate, and the second contact force provides the moving force for the mandibular jaw to move it to its corrected orientation.

This summary is intended to provide an overview of subject matter of the present patent application. It is not intended to provide an exclusive or exhaustive explanation of the invention. The detailed description is included to provide further information about the present patent application. The details of one or more aspects of the disclosure are set forth in the accompanying drawings and the description below. Other features, objects, and advantages and use of the invention will become apparent from the following detailed description and the accompanying drawings that illustrate the features of the invention.

BRIEF DESCRIPTION OF DRAWINGS

The following drawings are illustrative of particular embodiments of the present invention and therefore do not limit the scope of the invention. The drawings are not to scale and are intended for use in conjunction with the explanations in the following detailed description. Embodiments of the present invention will hereinafter be described in conjunction with the appended drawings. The drawings illustrate generally, by way of example, but not by way of limitation, various embodiments discussed in the present document.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 7:
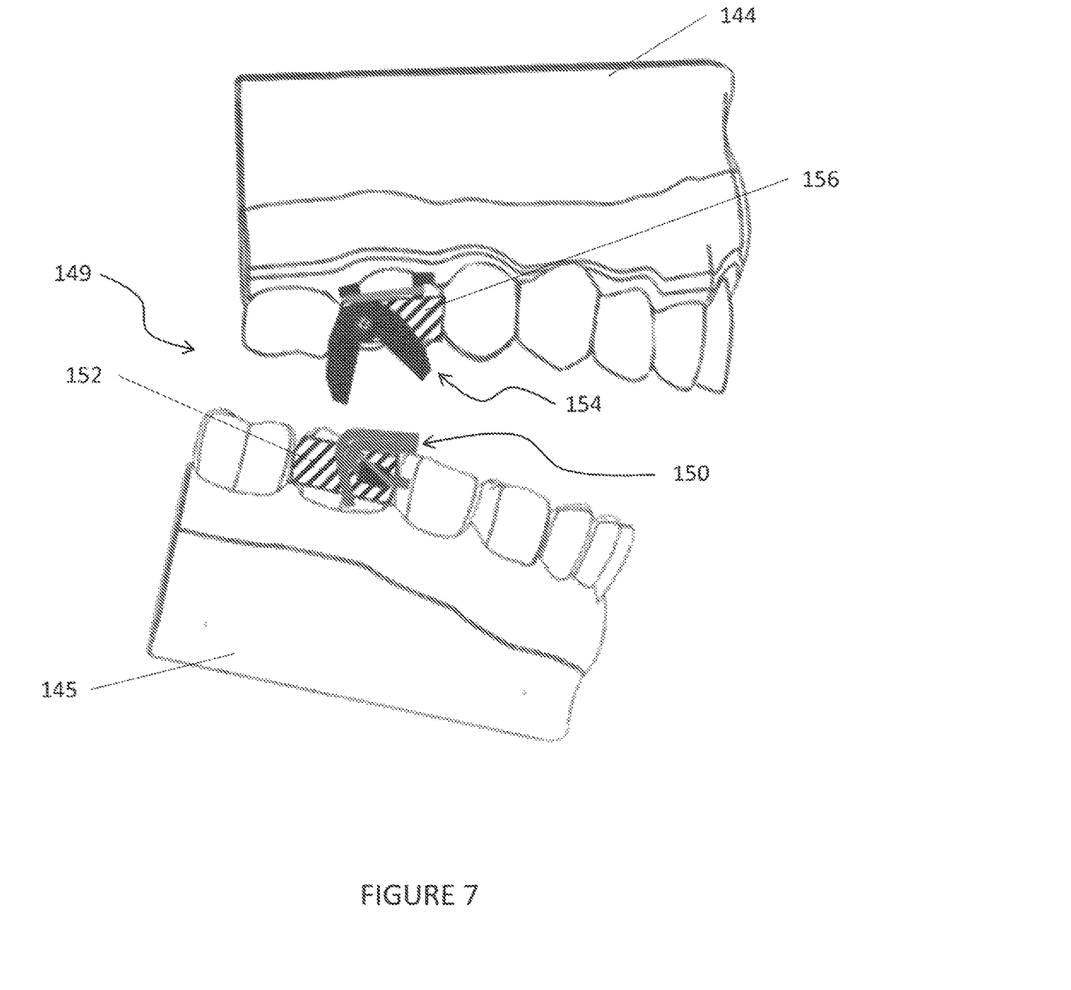
FIG. 7 illustrates an orthodontic appliance attached to open mandibular and maxillary jaws to correct Class II type malocclusion according to an embodiment of the invention.

An orthodontic appliance 149 is attached to mandibular 145 and maxillary 144 jaws as illustrated in FIG. 7 according to an embodiment of the invention to correct Class II type malocclusion. A first member 150 and a second member 154 of the orthodontic appliance 149 are attached to mandibular 145 and maxillary 144 jaws, respectively. A first anchoring element 152 is fixedly attached to the first molar of the mandibular jaw 145, and a second anchoring element 156 is fixedly attached to the first molar of the maxillary jaw 144. Anchoring elements can be bands or crowns that can be fitted over first molars. The first member 150 of the orthodontic appliance 149 is fixedly attached to the first anchoring element 152, and the second member 154 of the orthodontic appliance 149 is rotatingly coupled with the second anchoring element 156. Alternatively, in other embodiments, the first member and the second member of the orthodontic appliance can be attached to the mandibular and maxillary jaws via an archwire.

FIG. 7 illustrates the jaws, and the orthodontic appliance in open position. In this position, the first member and the second member of the orthodontic appliance are completely separated from each other. When the jaws are closed, for example during chewing, the first member and the second member of the orthodontic appliance contact each other, and the second member pushes the mandibular jaw in correct position relative to the maxillary jaw as it will be apparent in the future sections.

Figures 8, 9, 10, 11:
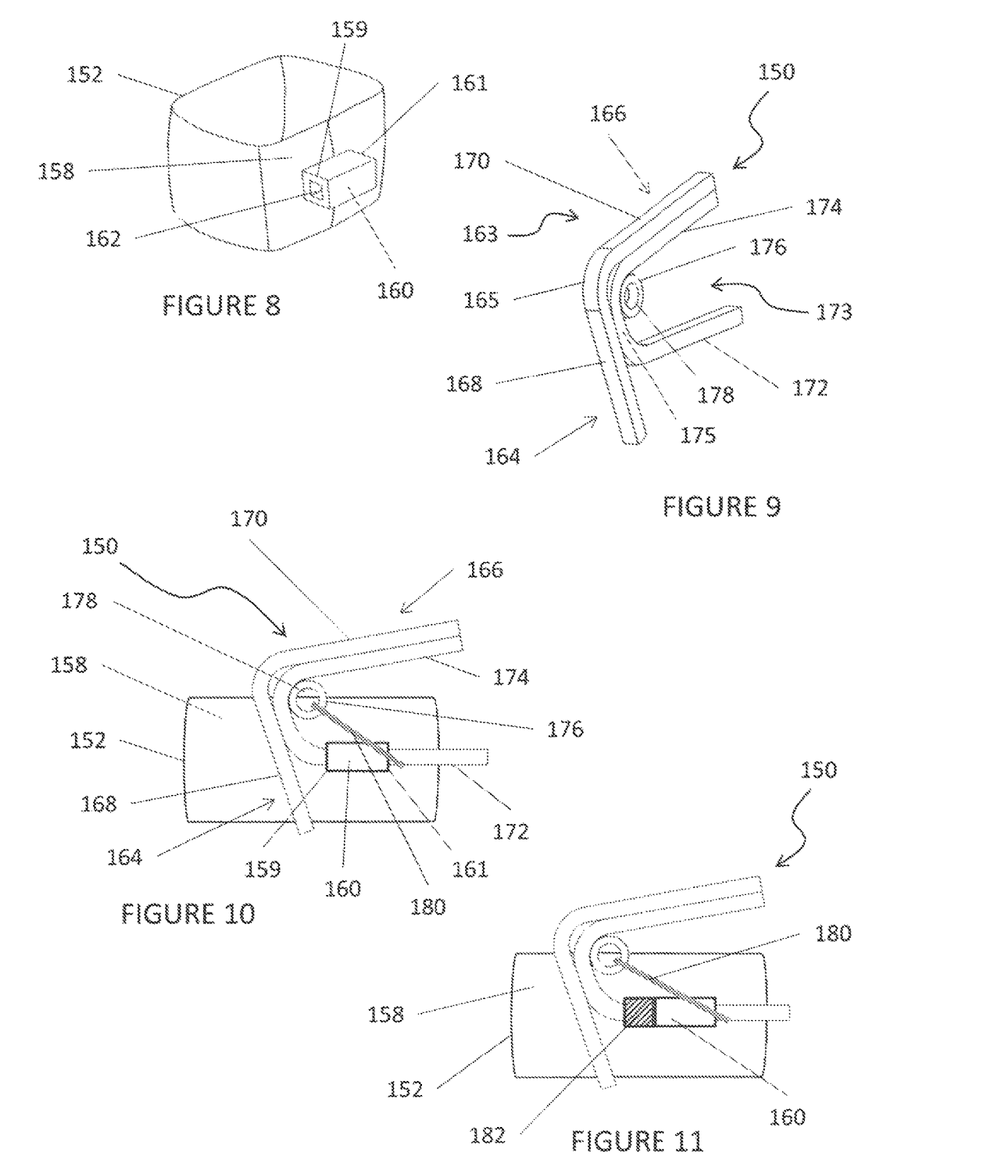
FIG. 8 includes the first anchoring element according to an embodiment of the invention.
FIG. 9 includes the first member of the orthodontic appliance according to an embodiment of the invention.
FIG. 10 illustrates the first member of the orthodontic appliance as attached to the first anchoring element according to an embodiment of the invention.
FIG. 11 illustrates the shim between the first member of the orthodontic appliance and the first anchoring element according to an embodiment of the invention.

The first anchoring element 152 is illustrated in FIG. 8 according to an embodiment of the invention. The first anchoring element 152 can be a band, and it is fixedly attached to the first molar of the mandibular jaw 145. A mounting element 160 can be fixedly attached to the buccal surface 158 of the first anchoring element 152. The mounting element 160 can have a rectangular cross-section extending buccally from the buccal surface 158 of the first anchoring element 152. The mounting element 160 is elongated in posterior direction. The mounting element 160 has an aperture 162.

The first member 150 of the orthodontic appliance 149 is illustrated in FIG. 9 according to an embodiment of the invention. The first member 150 includes a first part 163, a second part 173, and a first hook 176. The first part 163 and the second part 173 can be made of a square or rectangular wire form, and fixedly attached together. The first hook 176 can be made of sheet metal with a round, C, or J cross-section, and fixedly attached to the second part 173. Alternatively, in other embodiments, the first part 163,the second part 173, and the first hook 176 can be formed as integral part of the same component. the first part 163, the second part 173, and the first hook 176 can be made from any known engineering materials including stainless steel.

The first part 163 of the first member 150 consists of a first section 164, a second section 166, and a transition section 165 between the first section and the second section. The first section 164 is approximately perpendicular to the second section 166. The first surface 168 is located on the outer surface of the first section 164 away from the second part 173, and the second surface 170 is located on the outer surface of the second section 166 away from the second part 173. The first surface 168 and the second surface 170 can be straight or curved.

The second part 173 of the first member 150 consists of a first extension 172, a second extension 174, and a bridge section 175 between the first extension 172 and the second extension 174. The second extension 174 is fixedly attached to the second section 166 of the first part 163 on the surface of the second section 166 opposite the second surface 170. The bridge section 175 is fixedly attached to the first section 164 of the first part 163 on the surface of the first section 164 opposite the first surface 168. The first extension 172 of the second part 173 extends away from the first section 164 of the first part 163. The first extension 172 is approximately perpendicular to the first section 164 of the first part 163. The second part 173 provides additional stiffness for the first section 164 and the second section 166 of the first part 163, and it also provides attachment location between the first member 150 and the mounting element 160.

Attachment of the first member 150 to the mounting element 160 is illustrated in FIG. 10 according to an embodiment of the invention. The first extension 172 of the first member 150 can be inserted through the aperture 162 located on the mounting element 160. The first extension enters in to the mounting element 160 from its first face 159, and exits from the mounting element in second face 161. The first extension 172 can be partially located inside the mounting element 160. Cross-section of the aperture 162 can be approximately in the same shape as the cross-section of the first extension 172. Aperture 162 allows the first extension 172 to be inserted in to the mounting element 160 easily, however, it does not allow the first extension 172 rotate around the longitudinal axis of the mounting element 160 after it is inserted. A first tension member 180 can be inserted through the opening 178 of the hook 176, and it can be connected to the first extension 172 proximate the second face 161 of the mounting element 160 after the first extension 172 exits from the mounting element 160. The first tension member 180 can prevent the first member 150 from coming out of the mounting element 160. In other embodiments, a shim 182 can be located between the first member 150 and the mounting element 160 to vary the length of the first extension 172 inserted through the mounting element 160. This can allow an accurate control of the location of the first member 150 relative to the first mounting element 160.

The first member 150 can be fixedly attached to the first anchoring element 152 as explained in previous sections. This is an exemplary attachment method. There can be other attachment methods known to someone skilled in the art without changing the general intent of the invention.

Figure 12:
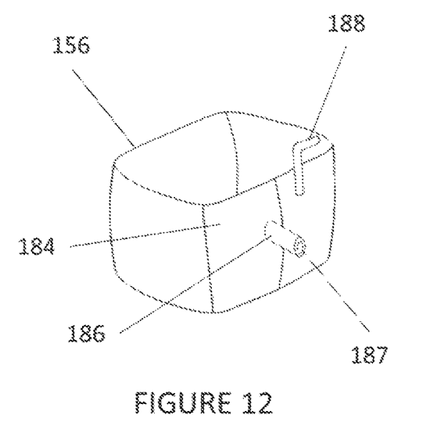
FIG. 12 illustrates the second anchoring element according to an embodiment of the invention.

The second anchoring element 156 of the orthodontic appliance 149 is illustrated in FIG. 12 according to an embodiment of the invention. The second anchoring element 156 can be a band, and it is fixedly attached to the first molar of maxillary jaw 144. A pin 186 is fixedly attached to the buccal surface 184 of the second anchoring element 156. Pin 186 extends buccally from the second anchoring element 156. Pin 186 has a round cross-section, and a threaded hole 187 can be formed on the tip of the pin 186. A second hook 188 is fixedly attached to the second anchoring element 156.

Figure 13:
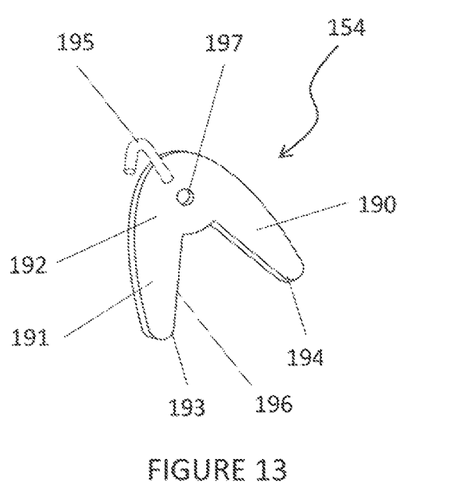
FIG. 13 illustrates the second member of the orthodontic appliance according to an embodiment of the invention.

The second member 154 of the orthodontic appliance 149 is illustrated in FIG. 13 according to an embodiment of the invention. The second member 154 includes a first arm 190, a second arm 191 and a body section 192. The first arm 190, the second arm 191, and the body section 192 can be formed as an integral part of the second member 154. Alternatively, the first arm 190, the second arm 191, and the body section 192 can be formed separately and fixedly attached together in an assembly operation to form the second member 154. Various known engineering materials including stainless steel can be used to form the second member 154. The first arm 190 is an elongated arm extending from the body section 192. Tip of the first arm 190 can be rounded. Tip of the first arm 190 creates the first contact point 194 that will interface with the second surface 170 of the first member 150 during the operation of the orthodontic appliance 149. The second arm 191 is an elongated arm extending from the body section 192 as well. Tip of the second arm 191 can be rounded. Tip and the inner edge of the second arm 191 facing the first arm 190 creates the second contact point 193 and contact edge 196, respectively. The second contact point 193 and the contact edge 196 interface with the first surface 168 of the first member 150 during the operation of the orthodontic appliance 149. The contact edge 196 can be formed in various shapes. It can be a straight edge, or curved edge depending on the desired contact between the first member 150 and the second member 154 of the orthodontic appliance 149. Alternatively, the contact edge 196 can be recessed to prevent contact over the contact edge 196 wherein contact between the second arm 191 of the second member 154 and the first surface 168 of the first member 150 can be provided over the second contact point 193 only. An aperture 197 can be formed in to the body section 192 of the second member 154. A third hook 195 can be fixedly attached to the second member 154.

The second member can be constructed in various ways. It can have a circular shape in general. A portion of the circle can be cut away to create the contact points 193 and 194.

Figure 14:
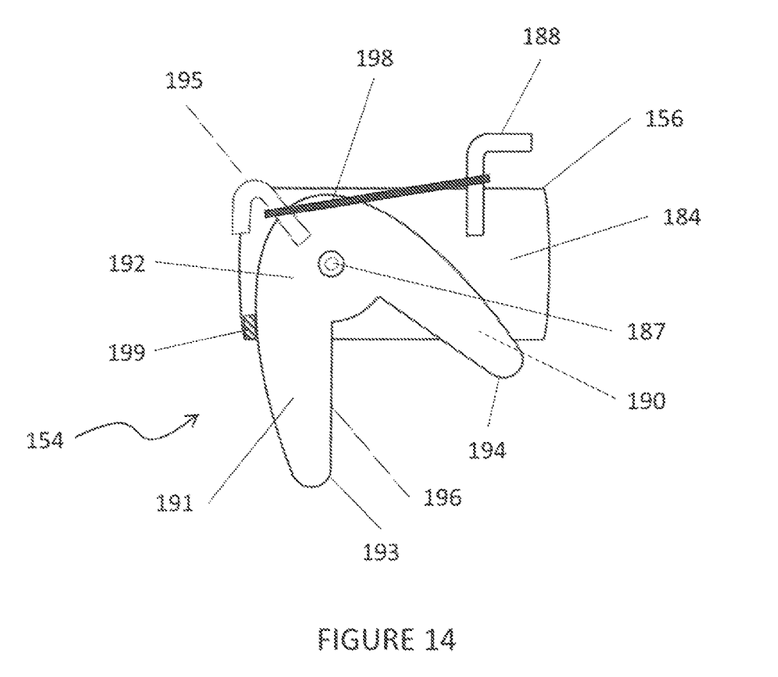
FIG. 14 illustrates the second member of the orthodontic appliance as attached to the second anchoring element according to an embodiment of the invention.

The second member 154 is rotatingly coupled with the second anchoring element 156. The second member 154 can be attached to the second anchoring element 156 as illustrated in FIG. 14 according to an embodiment of the invention. Pin 186 is inserted through the aperture 197. A screw (not shown) can be threadingly engaged with the pin through the threaded hole 187. Head of the screw can be slightly larger than the diameter of aperture 197, and thus, it prevents the second member 154 becoming disengaged from the second anchoring element 156.

A stop bracket 199 is fixedly attached to the second anchoring element 156. A second tension member 198 can be attached between the second hook 188 and the third hook 195. The second tension member 198 pulls the third hook 195 towards the second hook 188 after the assembly, and thus, biases the second member 154 towards the stop bracket 199. The second tension member 198 can be a rubber band.

Orthodontic appliance described in previous sections can also be used together with orthodontic wires. The first member and the second member can be designed to allow the use of archwire adjacent to the orthodontic appliance.

Figure 15:
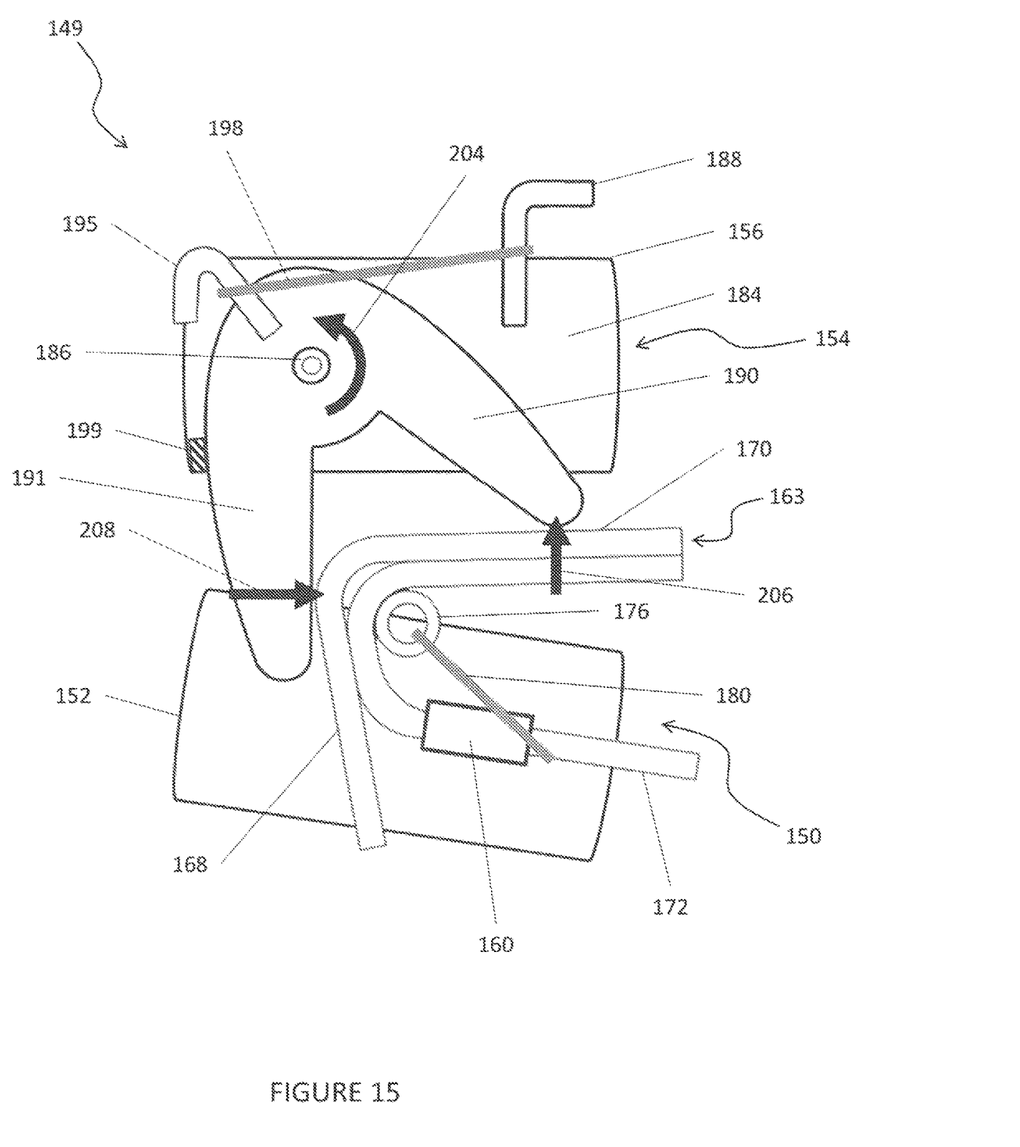
FIG. 15 illustrates two members of the orthodontic appliance in contact with each other at an intermediate jaw closure to correct Class II type malocclusion according to an embodiment of the invention.

A close-up view of the orthodontic appliance 149 is illustrated in FIG. 15 according to an embodiment of the invention. The first anchoring element 152, and the second anchoring element 156 are fixedly attached to the first molar of mandibular jaw 145 and maxillary jaw 144, respectively, as illustrated in FIG. 7. Mandibular and maxillary jaws are removed from FIG. 15 for clarity purposes. The first member 150 of the orthodontic appliance 149 is fixedly attached to the first anchoring element 152 as explained in the previous sections. The second surface 170 of the first member 150 is approximately parallel to the occlusal surfaces of teeth on mandibular jaw 145. The first member 150 of the orthodontic appliance is located proximate the buccal surfaces of teeth on the mandibular jaw. The second member 154 of the orthodontic appliance 149 is rotatingly coupled with the second anchoring element 156 as explained in previous sections. The second member 154 of the orthodontic appliance 149 is located proximate the buccal surfaces of teeth on maxillary jaw. The first member 150 and second member 154 of the orthodontic appliance 149 are in vertical alignment. In some embodiments, the first part 163 of the first member 150 can be made of a wider plate to allow some lateral movement of the mandibular jaw without losing the vertical alignment between the first member 150 and the second member 154 of the orthodontic appliance 149.

As the mandibular and maxillary jaws approach each other when patient attempts to close his/her jaws, contact is initiated between the first member 150 and the second member 154. Initial contact occurs over the second surface 170 of the first member 150. The first contact point 194 touches the second surface 170 as the jaws are closed, and a first contact force 206 is created. As the jaws continue to be closed, the first member 150 pushes on to the second member at the first contact point 194, and rotates the second member in a first direction 204. During this operation, contact point 194 moves towards the center of rotation 186 of the second member 154. As the second member 154 rotates in the first direction 204, the second tension member stretches without losing contact between the second hook 188 and the third hook 195. During the closure of jaws, a second contact between the first member 150 and the second member 154 of the orthodontic appliance 149 occurs over the first surface 168 of the first member 150. The second contact point 193 and contact edge 196 of the second member 154 contacts the first surface 168 of the first member and creates a second contact force 208. The second contact force 208 pushes the mandibular jaw in anterior direction until the jaws are completely closed. During this operation, the first contact point 194 and the first contact force 206 moves in posterior direction over the second surface 170, and the second contact point 193 and the second contact force 208 moves downwards over the first surface 168 of the first member 150.

When jaws are in open position, first member 152 and the second member 154 of the orthodontic appliance 149 is not in contact with each other as illustrated in FIG. 7. In this orientation, the second member 154 of the orthodontic appliance 149 is biased in a direction opposite to the first direction 204 by means of the second tension member 198. The second member 154 rotates in opposite direction to the first direction 204 with the effect of the second tension member 198 until it hits the stop bracket 199. Therefore, every time jaws are open, the second member returns to the same original position.

Figure 16:
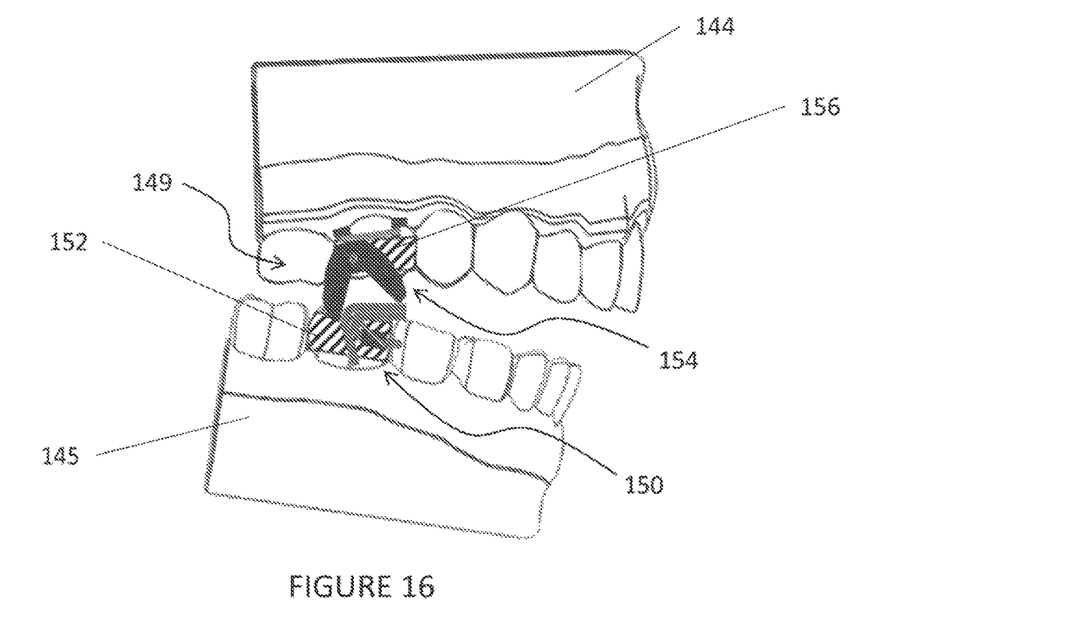
FIG. 16 illustrates an intermediate opening of jaws when two members of the orthodontic appliance initiate contact to correct Class II type malocclusion according to an embodiment of the invention.
Figure 17:
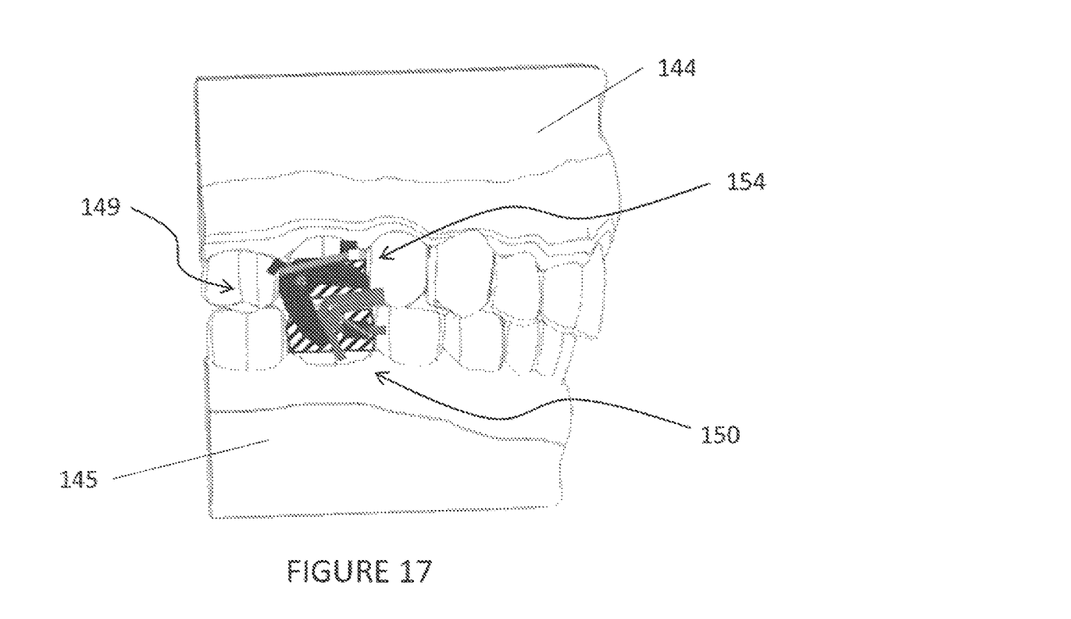
FIG. 17 illustrates two members of the orthodontic appliance interacting with each other over closed jaws to correct Class II type malocclusion according to an embodiment of the invention.

An orthodontic appliance 149 as attached to the mandibular and maxillary jaws is illustrated in FIG. 16 at an intermediate jaw closure according to an embodiment of the invention. When the mandibular jaw 145 is in uncorrected position as in the case of a Class II malocclusion, the second contact point 194 touches the second surface 170 of the first member 150, and the first contact point 193 touches the first surface 168 of the first member to activate the second member of the orthodontic appliance. As the jaws continue to be closed, the second member 156 rotates around the pin 186 and the first contact point 163 pushes the mandibular jaw 145 closer to its correct position as illustrated in FIG. 17. During this activation phase, the second contact point 194 moves posteriorly over the second surface 170, and the first contact point 193 slides downwards over the first surface 168. In some configurations, contact edge 196 may also come in contact with the first surface 168 during the activation phase. If the initial discrepancy between the uncorrected and the correct positions of the mandibular jaw is too big, it may not be possible to move the mandibular jaw the entire distance to its correct position in one operation. In that case, once the initial movement is completed, a shim 180 can be placed between the first member 150 and the mounting member 160 to attach the first member 150 on to the first anchoring element 152 in slightly posterior position to reactivate the second member and achieve additional correction of the position of mandibular jaw.

Figure 18:
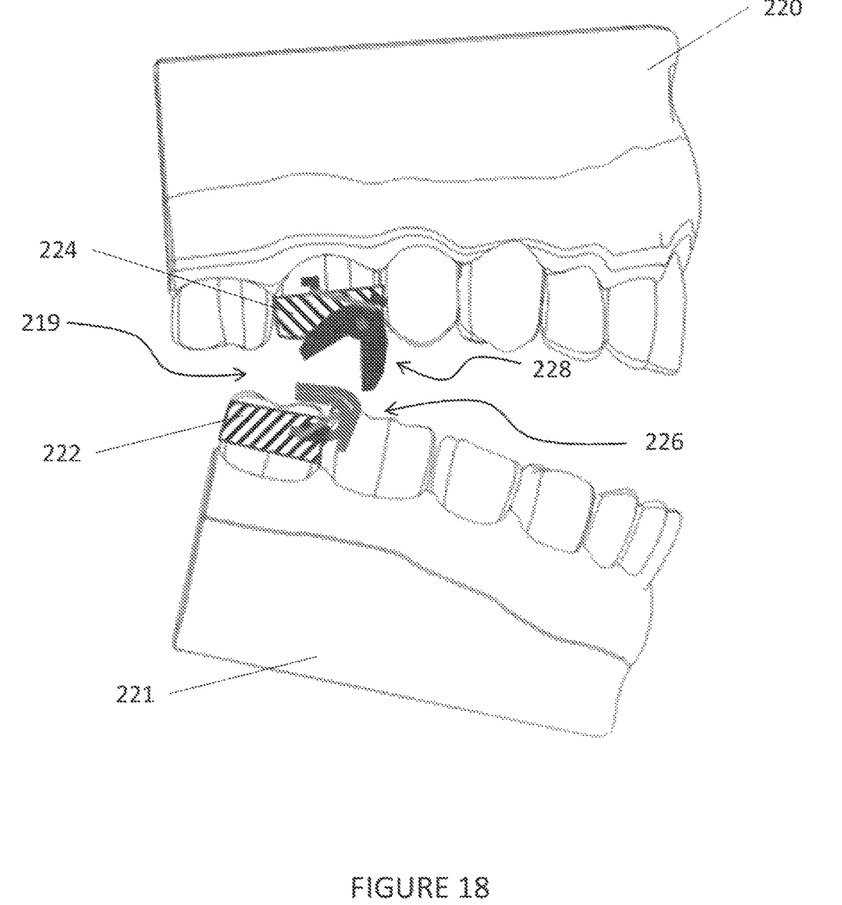
FIG. 18 illustrates two members of the orthodontic appliance attached to open jaws to correct Class III type malocclusion according to an embodiment of the invention.

An orthodontic appliance 219 is attached to a mandibular 221 and a maxillary 220 jaws in open position of jaws as illustrated in FIG. 18 according to an embodiment of the invention to correct Class III type malocclusions. A first anchoring element 222 is fixedly attached to the second molar of the mandibular jaw 221. A second anchoring element is fixedly attached to the first molar of the maxillary jaw 220. Anchoring elements may be attached to other teeth as required depending on the size of patient's mouth. A first member 226 of the orthodontic appliance 219 is fixedly attached to the first anchoring element 222. A second member 228 of the orthodontic appliance 219 is rotatingly coupled with the second anchoring element 224. As the jaws are closed, the first member 226 and the second member 228 of the orthodontic appliance 219 interact with each other to move the mandibular jaw 221 in posterior direction to its correct position relative to the maxillary jaw 220 to correct Class III malocclusion. This operation of the orthodontic appliance 219 will be explained in detail in the following sections.

Figure 19:
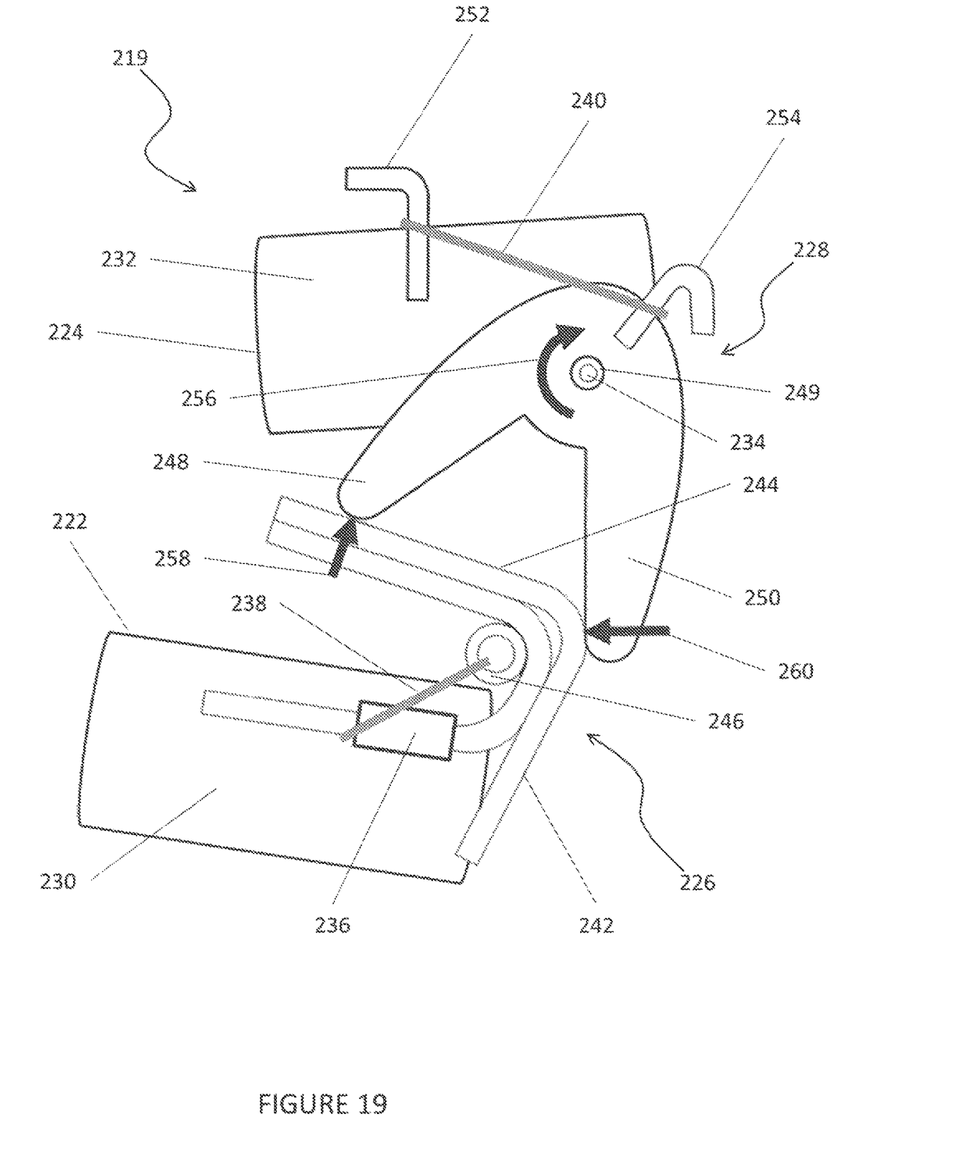
FIG. 19 illustrates two members of the orthodontic appliance in contact with each other at an intermediate jaw closure to correct Class III type malocclusion according to an embodiment of the invention.

A close-up view of the orthodontic appliance 219 is illustrated in FIG. 19 according to an embodiment of the invention. Jaws and teeth are removed from FIG. 19 for clarity purposes. The first anchoring element 222 is fixedly attached to the second molar of mandibular jaw 221 as illustrated in FIG. 18. A mounting element 236 is fixedly attached to the buccal surface 230 of the first anchoring element 222. The first member 226 of the orthodontic appliance 219 is fixedly attached to the mounting element 236. The first member 226 of the orthodontic appliance 219 can have a first surface 242, a second surface 244, and a first hook 246. A first tension member 238 is attached to the first hook 246 on its first end and attached to a portion of the first member 226 adjacent to the mounting element 236 on its second end to secure the first member to the mounting element.

The second anchoring element 224 is fixedly attached to maxillary jaw 220 as illustrated in FIG. 18. A second hook 252 and a pin 234 is fixedly attached to the buccal surface 232 of the second anchoring element 224. The second member 228 of the orthodontic appliance 219 is rotatingly coupled with the second anchoring element 224. The second member 228 of the orthodontic appliance 219 includes a first arm 248, a second arm 250, a third hook 254, and an aperture 249. Pin 234 is inserted through the aperture 249. Axis of the pin 234 forms the rotation axis of the second member 228. A screw can be threadingly engaged with the pin 234 after it is inserted through the aperture 249. The screw is not shown in FIG. 19. Head diameter of the screw can be larger than the diameter of the aperture 249 and prevents the second member 228 being disengaged from the second anchoring element 224. A second tension member 240 is attached to the second hook 252 on its first end, and attached to the third hook 254 on its second end. The second tension member 240 allows the second member 228 to rotate during the operation of the orthodontic appliance 219, and biases the second member 228 towards the original position of the second member 228 when there is no contact between the first member 226 and the second member 228.

When the jaws are closed, contact is initiated between the first arm 248 of the second member 228 and the second surface 244 of the first member 226 of the orthodontic appliance. A first contact force 258 created over the first arm 248 rotates it in the first direction 256, and thus, a second contact is created between the second arm 250 of the second member 228 and the first surface 242 of the first member 226. A second contact force 260 is created over the first surface 242 of the first member 226. The second contact force 260 pushes the first member 226, and thus, the mandibular jaw 221 in posterior direction. When the jaws are opened, second tension member 240 causes the second member 228 to rotate in a direction opposite to the first direction 256 to bring it to its original position.

Figure 20:
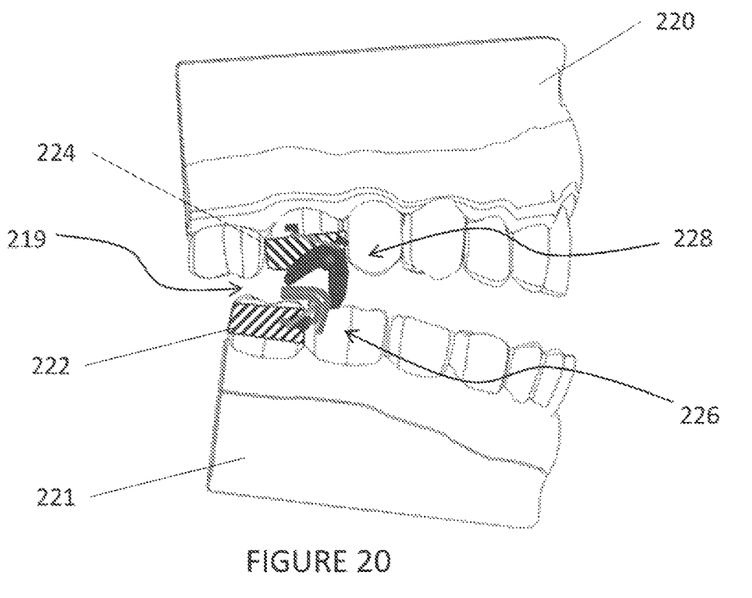
FIG. 20 illustrates an intermediate opening of jaws when two members of the orthodontic appliance initiate contact to correct Class III type malocclusion according to an embodiment of the invention.
Figure 21:
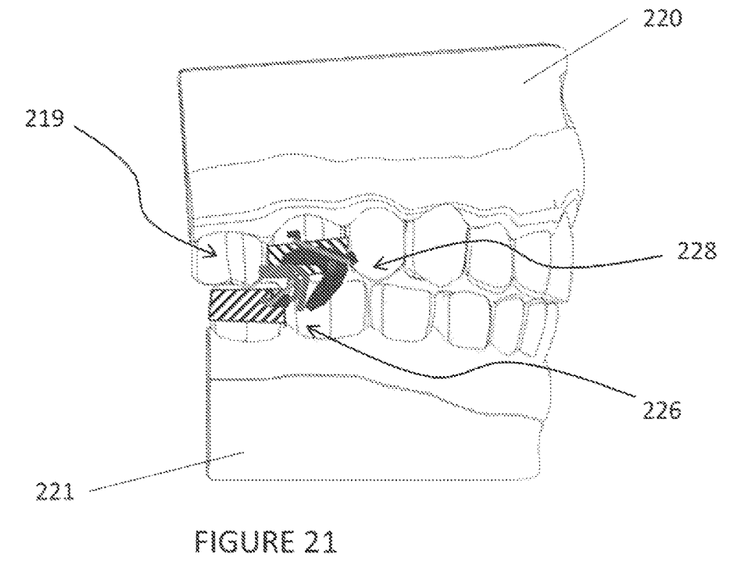
FIG. 21 illustrates two members of the orthodontic appliance interacting with each other over closed jaws to correct Class III type malocclusion according to an embodiment of the invention.

An orthodontic appliance 219 as attached to the mandibular and maxillary jaws is illustrated in FIG. 20 at an intermediate jaw closure according to an embodiment of the invention. When the mandibular jaw 221 is in uncorrected position as in the case of a Class III malocclusion, the second arm 248 touches the second surface 244 of the first member 226, and the first arm 250 touches the first surface 242 of the first member to activate the second member of the orthodontic appliance. As the jaws continue to be closed, the second member 228 rotates around the pin 234 and the first arm 250 pushes the mandibular jaw 221 closer to its correct position as illustrated in FIG. 21. During this activation phase, the contact point between the second arm 248 and the second surface 244 moves anteriorly over the second surface 244, and the contact point between the first arm 250 and the first surface 242 slides downwards over the first surface 242. If the initial discrepancy between the uncorrected and the correct positions of the mandibular jaw is too big, it may not be possible to push the mandibular jaw the entire distance to its correct position in one operation. In that case, once the initial movement is completed, a shim can be placed between the first member 226 and the mounting member 236 to attach the first member 226 on the first anchoring element 222 in slightly anterior position to reactivate the second member and achieve additional correction of the position of mandibular jaw.

Various embodiments of the orthodontic appliance illustrated in FIGS. 1-21 are described in previous sections as they are attached to the right side of patient's jaws. A mirror image of the orthodontic appliance can be also attached to the left side of patient's mouth. However, depending on the treatment method a single or dual attachments can be used.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. An orthodontic appliance for repositioning a mandibular jaw relative to a maxillary jaw, comprising:
   a first member adapted to be connected to one of the mandibular jaw or the maxillary jaw, the first member comprising;
      a first surface; and
      a second surface; wherein the second surface extends from the first surface in a transverse direction;
   a second member adapted to be rotatingly coupled with the other one of the mandibular jaw or the maxillary jaw; the second member comprising;
      a first arm; and
      a second arm a first tension member, connected to and configured to apply a force to the first member, and
      a second tension member connected to and configured to apply a biasing force to the second member;
   wherein the second member is in vertical alignment with the first member so that the second arm is configured to contact the second surface between an intermediate closure position of the jaws and a complete closure position of the jaws and cause the second member to rotate in a first direction thereby pressing the first arm against the first surface to exert a push force on to the mandibular jaw to reposition it relative to the maxillary jaw and wherein as the jaws open from the complete or intermediate closure position to a fully open position, the second member rotates due to the biasing force applied by the second tension member in a second direction opposite the first direction, and separates from the first member, such that the first and second member are not in contact with each other.

2. The orthodontic appliance of claim 1, wherein the first member further comprises:
   a first part; wherein the first surface and the second surface are formed as integral sections of the first part; wherein the second surface is configured to be parallel to the occlusal surfaces of the teeth when the mouth is in the fully open position;
   a second part comprising a first extension, a second extension, and a bridge section;
      wherein the first extension, the second extension, and the bridge section are formed as integral sections of the second part; and
   a hook; wherein the hook is fixedly attached to the first member;
   wherein the first part and the second part are fixedly attached to each other;
   wherein the first extension extends away in a transverse direction from the first surface.

3. The orthodontic appliance of claim 1, further comprising:
   a first anchor; wherein the first anchor is adapted to be fixedly attached to a first tooth located on one of the mandibular jaw or the maxillary jaw; and
   a second anchor; wherein the second anchor is adapted to be fixedly attached to a second tooth located on the other one of the mandibular jaw or the maxillary jaw.

4. The orthodontic appliance of claim 3, wherein the first anchor further includes a mount; wherein the mount is fixedly attached to the first anchor, and a first extension is connected to the mount.

5. The orthodontic appliance of claim 3, wherein the second anchor further comprises:
   a pin;
   a stop bracket; and
   a hook;
   wherein the pin, the stop bracket, and the hook are fixedly attached to the second anchor.

6. The orthodontic appliance of claim 1, wherein the second member further comprises:
   a body section connected to the first arm and the second arm; and
   a hook;
   wherein the hook is fixedly attached to the body section.

7. The orthodontic appliance of claim 6, wherein the body section further comprises an aperture; wherein a pin is inserted through the aperture.

8. The orthodontic appliance of claim 1, wherein at least one of the first member and the second member is adjustable in an anterior-posterior direction and lockable in a desired position.

9. The orthodontic appliance of claim 1, wherein the first tension member is attached to a first hook on one end and attached to a first extension on the other end.

10. The orthodontic appliance of claim 9, wherein the second tension member is attached to a second hook on one end and attached to a third hook on the other end.

11. The orthodontic appliance of claim 1, wherein the first surface and the second surface intersect to form a concave junction.

* * * * *